United States Patent [19]

Hahn

[11] Patent Number: 4,683,292

[45] Date of Patent: Jul. 28, 1987

[54] IMMUNOTHERAPEUTIC POLYPEPTIDE AGENTS WHICH BIND TO LYMPHOCYTE IMMUNOGLOBULIN FC RECEPTORS

[75] Inventor: Gary S. Hahn, San Diego, Calif.

[73] Assignee: Immunetech, Inc., San Diego, Calif.

[21] Appl. No.: 522,602

[22] Filed: Aug. 12, 1983

[51] Int. Cl.[4] .............................................. C07K 7/06
[52] U.S. Cl. .................................................... 530/328
[58] Field of Search ................................ 260/112.5 R

[56] References Cited

U.S. PATENT DOCUMENTS

| | | | |
|---|---|---|---|
| 3,778,426 | 12/1973 | Najjar | 260/112.5 R |
| 4,153,688 | 5/1979 | Dimicoli et al. | 260/112.5 R |
| 4,161,522 | 7/1979 | Hamburger | 260/112.5 R |
| 4,171,299 | 10/1979 | Hamburger | 260/112.5 R |
| 4,201,770 | 5/1980 | Stevens | 424/177 |
| 4,215,112 | 7/1980 | Goldstein et al. | 260/112.5 R |
| 4,223,016 | 9/1980 | Roy et al. | 260/112.5 R |
| 4,225,579 | 9/1980 | Kleinberg | 260/112.5 R |
| 4,284,537 | 8/1981 | Beachey | 260/6 |
| 4,341,755 | 7/1982 | Lindall | 424/1 |
| 4,369,138 | 1/1983 | Lindall | 260/112.5 R |
| 4,388,233 | 6/1983 | Bissell et al. | 548/159 |
| 4,407,948 | 10/1983 | Goodman et al. | 435/91 |
| 4,409,141 | 10/1983 | Noda et al. | 260/112.5 R |
| 4,409,144 | 10/1983 | Heinicke | 260/112.5 R |
| 4,415,493 | 11/1983 | Weigle et al. | 260/112.5 R |
| 4,436,874 | 3/1984 | Aspisi et al. | 525/327.1 |
| 4,454,121 | 6/1984 | Beachey | 260/112.5 R |
| 4,457,867 | 7/1984 | Ishida | 260/112.5 R |
| 4,474,757 | 10/1984 | Arnon et al. | 424/88 |
| 4,476,116 | 10/1984 | Anik | 260/112.5 R |
| 4,497,801 | 2/1985 | Hashimoto et al. | 260/112.5 R |

OTHER PUBLICATIONS

Proc. Nat. Acad. Sci., vol. 72, No. 6, pp. 2081–2083 (1975).
Molecular Immunology, vol. 19, No. 10, pp. 1245–1254 (1982).
Science, (1975) pp. 389–390, vol. 189.
Veretennikova et al., Int. J. Peptide Protein Res. 17, (1981) 430–435.
Plummer, et al., Fed. Proc. 42 713 (1983).
Hunninghake et al. Clin. Immunol Rev. 1 (3) 337 (1981–1982).
Hunsicker, J. Exp. Med. 150 413 (1979).
Johnson et al., (J. Immunol., 117, 1491 (1975)).
Boackle et al., (Nature, 282, 742 (1979)).
Prystowksy et al. (Biochemistry 20, 6349 (1981)).
Lukas et al. (J. Immunol. 127, 2555 (1981)).
Burton et al. Nature 288, 338 (1980).
Morgan et al. (Proc. Natl. Acad. Sci. USA 79, 5388 (1982)).
Ciccimarra et al. (Proc. Natl. Acad. Sci. USA 72 208 (1975)).

(List continued on next page.)

*Primary Examiner*—Delbert R. Phillips
*Attorney, Agent, or Firm*—Lyon & Lyon

[57] ABSTRACT

An active site peptide which blocks immune complex binding to Fc receptors, the peptide having an amino acid sequence selected from the group consisting of:

A-B-C-D-E-F-G-H-I-J-K-L-M-N-O-P, or a subgroup thereof, wherein
A is Arg, Lys, Orn, Gln, or His;
B is Ser, Thr, Ala, or Gly;
C is Thr, Ser, Ala, or Gly;
D is Thr, Ser, Ala, or Gly;
E is Lys, Arg, Orn or His;
F is Thr, Ser, Ala, or Gly;
G is Ser, Thr, Ala, or Gly;
H is Gly, Ala, Thr, Ser, Lys, Arg, or Orn
I is Pro, Val, Leu, Ile, or Ala;
J is Arg, Lys, Orn, or His;
K is Ala, Thr, Ser, or Gly;
L is Ala, Thr, Ser, or Gly;
M is Pro, Val, Leu, Ile, or Ala;
N is Glu, or Asp;
O is Val, Leu, Ile, or Ala;
P is Tyr, or Phe.

and pharmaceutically acceptable salts thereof.

1 Claim, 4 Drawing Figures

OTHER PUBLICATIONS

Stanworth Mol. Immunol. 19 1245 (1982).
Hamburger, Immunology 38, 78 (1979).
Biochem, J., 180 665 (1979).
Biochem, J., 181 623 (1979).
Barnett–Foster et al. Mol. Immunol 19 407 (1982).
Barnett–Foster et al. J. Immunol 120, 407 (1978).
Takatsu et al., J. Immunol 114 1838 (1975).
Dorrington et al. Immunol Rev. 41, 3 (1978).
Perex-Montfort Mol. Immunol 19 1113 (1982).
Kuehl et al. Science 210 978 (1980).
Goodwin Clin, Immunol Immunopath 15 106 (1980).
Stenson et al. Immunol 125 1 (1980).
Leung et al. J. Immunol 129 1742 (1982).
Fischer et al. J. Immunol 126 1452 (1981).
Klein et al. Immunol 48 337 (1983).
Goodwin et al. Cancer Immunol Immunother., 8, 3 (1980).
Samuelsson Science 220 568 (1983).
Weiss et al. J. Immunol 129 309 (1982).
Fantone, J. Pathol. 107 397 (1982).
Perex et al. Textbook Rheumatogoly, vol. 1, W. B. Saunders Philadelphia, 1981 pp. 179–194).
Dreisn et al. N. Engl. J. Med. 298 358 (1978).
Lawrence et al. N. Engl. J. Med. 302 1187 (1980).
Holdsworth J. Immunol 130 735 (1983).
Striker J. Exp. Med. 149, 127 (1979).
Kumar in Pathologic Basis of Disease eds. S. L. Robbins & R. S. Cotran (W. B. Saunders; Philadelphia, 1979), p. 304.
Melwicz et al., Clin. Exp. Immunol., 49, 364 (1982).
Spiegelberg, et al., 42, 124 (1983).
Scott et al., Fed. Proc., 42, 129 (1983).
McMillan, N. Engl. J. Med., 304, 1135 (1981).
Fehr et al. (N. Engl. J. Med., 306, 1254 (1982)).
Imbach et al. (Lancet, Jun. 6, 1981, p. 1228).
Oberbarnscheidt et al., Immunol., 35, 151 (1978).
Kolsch et al., Immunol. Rev., 49, 61 (1980).
Fridman et al., Immunol Rev. 56, 51 (1981).
Bich-Thuy, J. Immunol., 129, 150 (1982).
Smolen et al., J. Immunol., 129, 10150 (1982).
Goeken et al., Hum. Immunol., 6, 79 (1983).
Kabelitz et al., Eur. J. Immunol., 12, 687 (1982).
Sakane et al., Proc. Natl. Acad. Sci. U.S.A., 75, 3464 (1978).
Miyasaka et al., J. Clin. Invest., 66, 928 (1980).
James et al., J. Clin. Invest., 66, 1305 (1980).
Hodgkin's Lymphoma Engleman, et al., J. Clin. Invest., 66149 (1980).
Smith et al., J. Natl. Cancer Inst., 58, 579 (1977).
Cochrane et al., Lancet 1, 441 (1976).
Douvas, Ann. Immunol. Inst. Pasteur, 132C, 307 (1981).
Ulcerative Colitis Hibi et al., Clin. Exp. Immunol., 49, 75 (1982).
Hashimoto's Thyroiditis Calder et al., Clin. Exp. Immunol., 14, 153 (1973).
Gonzalez-Molina et al., J. Clin. Invest., 59, 616 (1977).
Merrifield J. Am. Chem. Soc., 85, 2149–2154 (1963).
Barry & Merrifield in the Peptides eds. E. Gross & F. Meinehofer, Vol. 2 (Academic press, 1980) pp. 2, 285.
Synthesis of a Tetrapeptide by R. B. Merrifield, Journal of American Chemical Society, Vol. 85, pp. 2, 2154 (1963).

IMMUNOTHERAPEUTIC POLYPEPTIDE AGENTS WHICH BIND TO LYMPHOCYTE IMMUNOGLOBULIN FC RECEPTORS

BACKGROUND OF THE INVENTION

Antibody synthesis is a defense response of higher vertebrates. The molecular entities which stimulate antibody synthesis (e.g., a virus particle) are called antigens. The introduction of an antigen into the body of a higher vertebrate stimulates specific white blood cells, B lymphocytes, to produce antibodies that combine specifically with the antigen to prevent its further multiplication, or to otherwise inactivate it. The study of antibodies and their action with antigens is a branch of immunology.

Antibodies which circulate in blood or other body fluids are termed humoral antibodies, as distinguished from "membrane antibodies" which remain bound to their parent lymphocytes. The term immunoglobulin is used to generically refer to all antibodies. In humans, all immunoglobulins are divided into five classes termed IgG, IgA, IgM, IgD and IgE. Each immunoglobulin molecule consists of two pairs of identical polypeptide chains. The larger pair termed "heavy chains" and designated gamma ($\gamma$), alpha ($\alpha$), mu ($\mu$), delta ($\delta$) and epsilon ($\epsilon$), respectively, are unique for each immunoglobulin class and are linked together by disulfide (s—s) bonds between each chain. Each heavy chain consists of about 400 to 500 amino acid residues linked together by polypeptide bonds. Each light chain, by contrast, consists of about 200 amino acids and are usually linked to a heavy chain by a single disulfide bond.

In 1969, Gerald Edelman first determined the amino acid sequence of an entire human IgG molecule. He found that both heavy and light chains are organized into homology units or "domains" about 100 amino acids in length. Subsequent sequence analysis of the other four immunoglobulin classes demonstrate that they are also organized into structurally similar domains having different amino acid sequences. The first or amino-terminal domain of both light and heavy chains have discrete regions within which considerable variation in amino acids occur. These domains are therefore termed variable (V) domains and are designated $V_H$ in heavy chains and $V_L$ in light chains.

The molecular association of a $V_L$ and $V_H$ domain within an intact immunoglobulin forms an antigen-combining site which may bind to a specific antigen with high affinity. The domain structure of all light chains is identical regardless of the associated heavy chain class. Each light chain has two domains, one $V_L$ domain and one domain with a relatively invariant amino acid sequence termed constant, light or $C_L$.

Heavy chains, by contrast may have either three (IgG, IgA, IgD) or four (IgM, IgE) constant or C domains termed $C_H1$, $C_H2$, $C_H3$, and $C_H4$ and one variable domain, termed $V_H$. Alternatively, C domains may be designated according to their heavy chain class; thus $C_\epsilon 4$ indicates the $C_H4$ domain of the IgE (epsilon) heavy chain.

Figure 1:
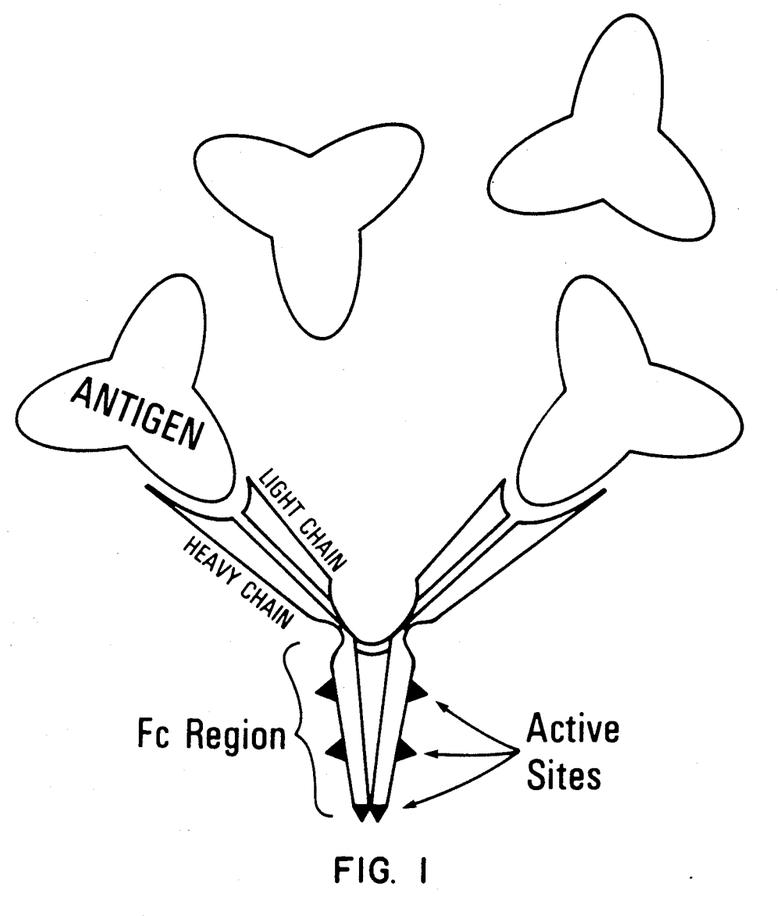
FIG. 1 is a schematic illustration of antigens bound to an antibody. The light and heavy chains of the antibody's Fab arms, and the biologically active sites of the Fc region are shown.

Visualization of antibodies by electron microscopy or by x-ray diffraction reveals that they have a "Y" shape. IgA and IgM antibodies, in addition, combine in groups of two and five, respectively, to form dimers and pentamers of the basic Y shaped antibody monomer. See FIG. 1.

When antibodies are exposed to proteolytic enzymes such as papain or pepsin, several major fragments are produced. The fragments which retain antigen-binding ability consist of the two "arms" of the antibody's Y configuration and are termed Fab (fragment-antigen binding) or Fab'2 which represent two Fab arms linked by disulfide bonds. The other major fragment produced constitutes the single "tail" or central axis of the Y and is termed Fc (fragment-crystalline) for its propensity to crystallize from solution. The Fc fragment of IgG, A, M, and D consists of dimers of the two carboxy-terminal domains of each antibody (i.e., $CH_H2$ and $C_H3$ in IgG, IgA and IgD, and $C_H3$ and $C_H4$ in IgM.) The IgE Fc fragment, by contrast, consists of a dimer of its three-carboxy-terminal heavy chain domains ($C_\epsilon 2$, $C_\epsilon 3$ and $C_\epsilon 4$).

Figure 2A:
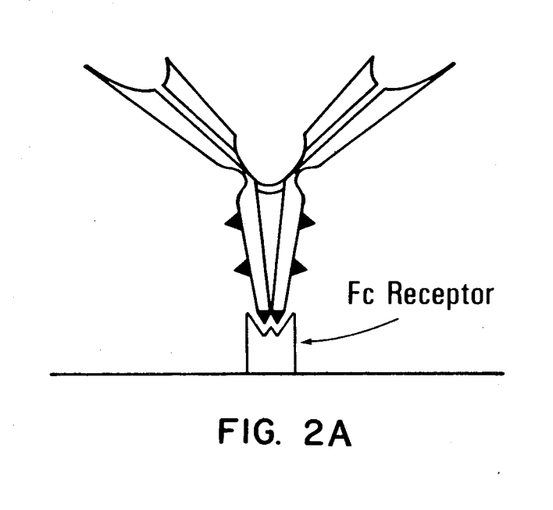
FIG. 2(a) is a schematic illustration of an antibody bound, via its Fc region active site, to a cellular Fc receptor.

The Fc fragment contains the antibody's biologically "active sites" which enable the antibody to "communicate" with other immune system molecules or cells and thereby activate and regulate immune system defensive functions. Such communication occurs when active sites within antibody regions bind to molecules termed Fc receptors. See FIG. 2A.

Fc receptors are molecules which bind with high affinity and specificity to molecular active sites within immunoglobulin Fc regions. Fc receptors may exist as integral membrane proteins within a cell's outer plasma membrane or may exist as free, "soluble" molecules which freely circulate in blood plasma or other body fluids.

Each of the five antibody classes have several types of Fc receptors which specifically bind to Fc regions of a particular class and perform distinct functions. Thus IgE Fc receptors bind with high affinity to only IgE Fc regions or to isolated IgE Fc fragments. It is known that different types of class-specific Fc receptors exist which recognize and bind to different locations within the Fc region. For example, certain IgG Fc receptors bind exclusively to the second constant domain of IgG ($C_H2$), while Fc receptors mediating other immune functions bind exclusively to IgG's third constant domain ($C_H3$). Other IgG Fc receptors bind to active sites located in both $C_H2$ and $C_H3$ domains and are unable to bind to a single, isolated domain.

Once activated by antibody Fc region active sites, Fc receptors mediate a variety of important immune killing and regulatory functions. Certain IgG Fc receptors, for example, mediate direct killing of cells to which antibody has bound via its Fab arms (antibody-dependent cell mediated cytotoxicity—(ADCC)). Other IgG Fc receptors, when occupied by IgG, stimulate certain white blood cells to engulf and destroy bacteria, viruses, cancer cells or other entities by a process known as phagocytosis. Fc receptors on certain types of white blood cells known as B lymphocytes regulate their growth and development into antibody-secreting plasma cells. Fc receptors for IgE located on certain white cells known as basophils and mast cells, when occupied by antigen-bridged IgE, trigger allergic reactions characteristic of hayfever and asthma.

Certain soluble Fc receptors which are part of the blood complement system trigger inflammatory responses able to kill bacteria, viruses and cancer cells. Other Fc receptors stimulate certain white blood cells to secrete powerful regulatory or cytotoxic molecules known generically as lymphokines which aid in immune defense. These are only a few representative examples of the immune activities mediated by antibody Fc receptors.

It is only after antibodies bind to antigen or are otherwise caused to aggregate that active sites within the Fc region are able to bind to and activate Fc receptors. Fc receptors are, therefore, the critical link between antibodies and the remainder of the immune system. Fc receptor binding to antibody Fc region active sites may thus be characterized as the "final common pathway" by which antibody functions are mediated. If an antigen-bound antibody does not bind to an Fc receptor, the antibody is unable to activate the other portions of the immune system and is therefore rendered functionally inactive.

Figure 2B:
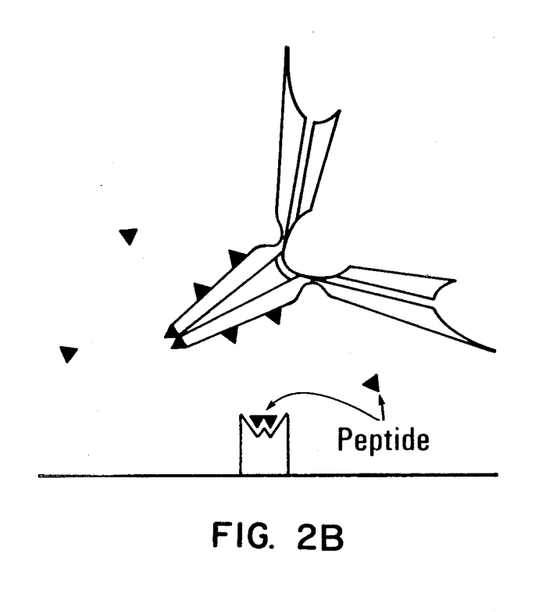
FIG. 2(b) is a schematic illustration of active site peptides which bind to and block, the antibody's Fc receptor, thus preventing the antibody's immunological activity. Such Fc receptor blockage forms the basis of the present invention.

Any peptide with the ability to bind to immunoglobulin Fc receptors has therapeutic usefulness as an immunoregulator by virtue of the peptide's ability to regulate binding to the receptor. Such an Fc receptor "blocker" occupies the immunoglobulin-binding site of the Fc receptor and thus "short circuits" the immunoglobulin's activating ability. FIG. 2B.

SUMMARY OF THE INVENTION

Most of the amino acids which make up antibodies function as molecular "scaffolding" which determine the antibody's structure, a highly regular three-dimensional shape. It is this scaffolding which performs the critical function of properly exposing and spatially positioning antibody active sites which consist of several amino acid clusters. A particular active site, depending upon its function, may already be exposed and, therefore, able to bind to cellular receptors. Alternatively, a particular active site may be hidden until the antibody binds to an antigen, whereupon the scaffolding changes orientation and subsequently exposes the antibody's active site. The exposed active site then binds to its specific Fc receptor located either on a cell's surface or as part of a soluble molecule (e.g., complement) and subsequently triggers a specific immune activity.

Since the function of an antibody's "scaffolding" is to hold and position its active sites for binding to cells or soluble molecules, the antibody's active sites, when isolated and synthesized as peptides, can perform the immunoregulatory functions of the entire antibody molecule.

Depending upon the particular type of Fc receptor to which an active site peptide binds, the peptide may either stimulate or inhibit immune functions. Stimulation may occur if the Fc receptor is of the type that becomes activated by the act of binding to an Fc region or, alternatively, if an Fc active site peptide stimulates the receptor. The type of stimulation produced may include, but is not limited to, functions directly or indirectly mediated by antibody Fc region-Fc receptor binding. Examples of such functions include, but are not limited to, stimulation of phagocytosis by certain classes of white blood cells (polymorphonuclear neutrophils, monocytes and macrophages; macrophage activation, antibody-dependent cell mediated cytotoxicity (ADCC); natural killer (NK) cell activity; growth and development of B and T lymphocytes and secretion by lymphocytes of lymphokines (molecules with killing or immunoregulatory activities).

The ability to stimulate immune system functions, including those listed above, is known to be therapeutically useful in treating diseases such as infectious diseases caused by bacteria, viruses or fungi, conditions in which the immune system is deficient due either to congenital or acquired conditions, cancer and many other afflictions of human beings or animals. Such immunostimulation is also useful to boost the body's protective cellular and antibody response to certain injected or orally administered substances administered as vaccines. This list is not intended to be all inclusive and merely provides representative examples of diseases or conditions in which immune stimulation has established therapeutic usefulness.

Inhibition of immune system functions may occur if an active site peptide binds to a particular Fc receptor which is not activated by the mere act of binding to an Fc region. Such Fc receptors normally become "activated" only when several Fc regions within an antigen-antibody aggregate or immune complex simultaneously bind to several Fc receptors, causing them to become "crosslinked". Such Fc receptor crosslinking by several Fc regions appears to be the critical signal required to activate certain types of Fc receptors. By binding to and blocking such an Fc receptor, an active site peptide will prevent Fc regions within immune complexes or antigen-antibody aggregates from binding to the receptor, thus blocking Fc receptor activation. See FIG. 2B.

The ability to inhibit immune system functions is known to be therapeutically useful in treating diseases such as allergies, autoimmune diseases including rheumatoid arthritis and systemic lupus erythematosis, certain types of kidney diseases, inflammatory bowel diseases such as ulcerative colitis and regional enteritis (Crohn's disease), certain types of inflammatory lung diseases such as idiopathic pulmonary fibrosis and hypersensitivity pneumonitis, certain types of demylinating neurologic diseases such as multiple sclerosis, autoimmune hemolytic anemias, idiopathic (autoimmune) thrombocytopenic purpura, certain types of endocrinological diseases such as Grave's disease or Hashimoto's thyroiditis and certain types of cardiac disease such as rheumatic fever. Immunosuppression is also therapeutically useful in preventing the harmful immune "rejection" response which occurs with organ transplantation or in transplantation of bone marrow cells used to treat certain leukemias or aplastic anemias. This list is not intended to be all inclusive but merely provides representative examples of diseases or conditions in which immunosuppression is known to be therapeutically useful.

DETAILED DESCRIPTION OF KNOWN ACTIVE SITE PEPTIDES

In the following sections, the amino acid components of the peptides are identified as abbreviations for convenience. These abbreviations are intended to include both the D- and L-forms although the L-form is preferred:

| Amino Acid | Abbreviation |
| --- | --- |
| L-glycine | GLY |
| L-alanine | ALA |
| L-valine | VAL |
| L-leucine | LEU |
| L-isoleucine | ILE |
| L-proline | PRO |
| L-methionine | MET |
| L-cysteine | CYS |
| L-phenylalanine | PHE |
| L-tyrosine | TYR |
| L-tryptophan | TRP |
| L-histadine | HIS |
| L-lysine | LYS |
| L-arginine | ARG |
| L-aspartic acid | ASP |
| L-asparagine | ASN |
| L-glutamic acid | GLU |
| L-glutamine | GLN |
| L-serine | SER |
| L-threonine | THR |
| L-ornithine | ORN |
| Carbobenzoxyl-amino acid | Z - amino acid |
| N—acetyl-amino acid | Ac - amino acid |

I. COMPLEMENT BLOCKING PEPTIDES

The classical pathway for complement activation consists of a group of blood plasma proteins which are activated to form a biochemical cascade beginning with the first complement component, C1 and ending with a cellular "attach complex" consisting of C5, C6, C7, C8 and C9. The pattern of activation is highly specific and begins when C1 binds to Fc region active sites within antibody-antigen complexes of either IgG or IgM. A molecular subunit of C1, termed C1q, contains six identical Fc receptors for IgG or IgM. C1q is an example of a "soluble" Fc receptor that exerts its bioactivity (complement activation resulting in cell lysis and inflammation) without being anchored to a cell surface membrane. The amino acid residues which contribute to the Fc active site for C1q in human IgG have been localized to the $C_H2$ domain. Johnson and Thames (J. Immunol., 117, 1491 (1975)) and Boackle, Johnson and Caughman (Nature, 282, 742 (1979)) found that peptides with sequences derived from the $C_H2$ of human IgG1 at aa 274–281 (Lys-Phe-Asn-Trp-Tyr-Val-Asp-Gly) had substantial complement activating ability when the peptides were adsorbed to erythrocytes. In particular, one peptide with the aa (amino acid sequence) (Lys-Ala-Asp-Trp-Tyr-Val-Asp-Gly) was about as effective in activating C1q-mediated cell lysis as immune complexes formed by heat aggregated IgG. The aforementioned researchers attributed this activity to the peptide's ability to act as an active binding site for the C1q Fc receptor. Other synthetic peptides with sequences derived from this region of IgG or from the aa 487–491 region of $C_H4$ of IgM (Glu-Trp-Met-Gln-Arg), e.g.

Lys—Phe—Asp—Trp—Ala—Val—Asp—Gly

Lys—Phe—Glu—Trp—Tyr—Val—Glu—Gly—Val—Glu—

Val—His—Glu—Ala—Lys—Ala—Lys—Pro—Gly—Arg

Trp—Tyr—Val—Asp—Gly

Lys—Tyr—Asp—Trp—Tyr—Val—Asp—Gly

Tyr—Asp—Tyr—Tyr—Val—Asp—Gly

Lys—Phe—Asp—Ala—Tyr—Val—Asp—Gly

Z—Val—Glu—Trp—Gly

Tyr—Val—Glu—Trp—Gly—Glu—Arg—Gly

Glu—Trp—Tyr—Glu—Arg—Gly

Z—Asn—Trp—Tyr—Val

Tyr—Glu—Arg—Gly

Z—Glu—Trp—Tyr—Glu—Arg—Gly
                              |
                             Tos were less active, while Trp-Leu and Tyr-Glu-Ala-Gly were inactive.

Subsequently, Prystowsky, et al. (Biochemistry, 20, 6349 (1981)), and Lukas, et al. (J. Immunol., 127, 2555 (1981)) demonstrated that peptides from an immediately adjacent $C_H2$ region from aa 281 to 292 were inhibitors of C1-mediated hemolysis. Specifically, peptides identical to IgG, $C_H2$ residues 281–290 (Gly-Val-Gln-Val-His-Asn-Ala-Lys-Thr-Lys) and aa282–292 (Val-Gln-Val-His-Asn-Ala-Lys-Thr-Lys-Pro-Arg-OH) were approximately as active as inhibitors as intact monomeric IgG. Other peptides, viz. aa275–290 (Phe-Asn-Trp-Tyr-Val-Asp-Gly-Val-Gln-Val-His-Asn-Ala-Lys-Thr-Lys), aa275–279 (Ac-Phe-Asn-Trp-Tyr-Val), aa289–292 (Thr-Lys-Pro-Arg) were less active.

Other investgators (Burton, et al., Nature, 288, 338 (1980), using other criteria, have concluded that the IgG, C1q-binding site is located among $C_H2$ residues aa316–340. They have, however, not reported on complement blocking activities of peptides from this region.

II. IMMUNOSTIMULATORY ACTIVE SITE PEPTIDES FROM IgG

A. Tuftsin

Tuftsin is a tetrapeptide, with sequence Thr-Lys-Pro-Arg, and is present in the second constant domain of all human IgG subclasses and in guinea pig IgG at aa 289–292. It was originally isolated from proteolytic digests of IgG by Najjar who found it to stimulate phagocytosis by granulocytes, monocytes and macrophages in vitro and is described in U.S. Pat. No. 3,778,426. Subsequent studies have shown Tuftsin to be active at nanomolar concentrations in many species including humans, cows, dogs, rabbits, guinea pigs and mice. In addition to its phagocytosis stimulating ability, Tuftsin has been shown to stimulate ADCC, Natural Killer (NK) cell activity, macrophage-dependent-T-cell education and antibody synthesis to T-cell-dependent and independent antigens in vitro and in vivo. Tuftsin is believed to act by binding to stereospecific receptors on granulocytes, macrophages and lymphocytes. Analysis of these receptors indicate that they resemble IgG Fc receptors in both number and ligand dissociation constants. Recent studies by Ratcliffe and Stanworth (Immunol. Lett., 4, 215 (1982)) and ourselves demonstrate that Tuftsin does bind to IgG Fc receptors since it competitively inhibits human IgG binding to human monocyte IgG Fc receptors. Tuftsin's immunostimulatory abilities are thus attributed to its ability to bind to immunoglobulin Fc receptors.

B. Rigin

Rigin is a tetrapeptide analogue of Tuftsin located in the peptide region of human IgG which spans the $C_H2$ and $C_H3$ domains at aa 341–345 having sequence Gly-Gln-Pro-Arg. (Veretennikova, et al., Int. J. Peptide Protein Res., 17, 430 (1981)). It has phagocytosis-stimulating abilities similar to those of Tuftsin and is described in U.S. Pat. No. 4,353,823.

C. Twenty-Four Residue Immunostimulatory Peptide

In 1982, Morgan, Huguli and Weigle (Proc. Natl. Acad. Sci. USA, 79, 5388 (1982)) reported the sequence of a 24 residue peptide identical to IgG aa 335–358 with the ability to nonspecifically activate lymphocytes. The peptide was shown to induce polyclonal B cell proliferation, antigen-specific antibody responses and Natural Killer (NK) cell-mediated lysis. This peptide (Thr-Ile-Ser-Lys-Ala-Lys-Gly-Gln-Pro-Arg-Glu-Pro-Gln-Val-Tyr-Thr-Leu-Pro-Ser-Arg-Glu-Glu-Met) and the 23 residue peptide lacking the carboxy-terminal methionine probably acts by binding to lymphocyte Fc receptors for IgG.

III. IgG-Derived Fc Receptor Blocking Peptides

A. Decapeptide—From $C_H3$ of Human IgG

In 1975, Ciccimarra, et al. (Proc. Natl. Acad. Sci. USA, 72, 2081 (1975)) reported the sequence of a decapeptide from human IgG which could block IgG binding to human monocyte IgG Fc receptors. This peptide is identical to IgG aa 407–416 (Tyr-Ser-Lys-Leu-Thr-Val-Asp-Lys-Ser-Arg). Stanworth, by contrast, was not able to demonstrate that this peptide could block monocyte IgG binding. He did, however, show that the peptide blocked human IgG binding to macrophage IgG Fc receptors of mice (Stanworth, Mol. Immunol., 19, 1245 (1982)).

B. Heptapeptide from $C_H2$ of Human IgG

In 1982, Ratcliffe and Stanworth (Immunol. Lett., 4, 215 (1982)) demonstrated that a peptide identical to IgG aa 295–301 (Gln-Tyr-Asp-Ser-Thr-Tyr-Arg) could slightly block IgG binding to human monocyte IgG Fc receptors. By contrast, a related peptide identical to IgG, $C_H2$, residues at aa 289–301 had no monocyte IgG blocking activity.

IV. IgE Fc Receptor Blocking Peptides

A. Human IgE Pentapeptide (HEPP)

In 1975, Hamburger reported that a pentapeptide with sequence derived from human IgE $C_\epsilon 3$ at aa 320–324 (Asp-Ser-Asp-Pro-Arg) could inhibit a local cutaneous allergic reaction (Prausnitz-Küstner) by approximately 90%. (Hamburger, Science, 189, 389 (1975) and U.S. Pat. Nos. 4,171,299 and 4,161,322.) This peptide has subsequently been shown to inhibit systemic allergic disease in humans after injection by the subcutaneous route. Recent studies demonstrate that the peptide has significant affinity for the IgE Fc receptor of human basophils and can block human IgE binding to basophil IgE Fc receptors by up to 70% (Plummer, et al., Fed. Proc., 42, 713 (1983)). The observed ability of this peptide to block systemic allergic disease in humans is attributed to the peptide's ability to bind to cellular IgE Fc receptors. (Hamburger, Adv. Allergology Immunol. (Pergamon Press: New York, 1980), pp. 591–593.

B. Hexapeptide from Human IgE

In 1979 Hamburger reported that a hexapeptide derived from $C_\epsilon 4$ at aa 476–481 (Pro-Asp-Ala-Arg-His-Ser) could block human IgE-binding to IgE Fc receptors on a human lymphoblastoid cell line (wil-2wt) (Hamburger, Immunology, 38, 781 (1979)). This peptide had been previously implicated as an agent useful in blocking IgE-binding to human basophil IgE Fc receptors (U.S. Pat. No. 4,161,522).

V. OTHER BIOLOGICALLY ACTIVE PEPTIDES FROM HUMAN IgE

In 1982, Stanworth (Mol. Immunol., 19, 1245 (1982)) reported that a decapeptide with sequence identical to a portion of $C_\epsilon 4$ of human IgE at aa 505–515 (Val-Phe-Ser-Arg-Leu-Glu-Val-Thr-Arg-Ala-Glu) caused a marked enhancement of binding of $^{125}$I-human IgG to mouse macrophages. Interaction of this peptide with Fc receptors, however, was not demonstrated.

In 1979 Stanworth, et al. demonstrated that certain peptides with sequences identical to portions of $C_\epsilon 4$ of human IgE, viz. aa 495–506 (Pro-Arg-Lys-Thr-Lys-Gly-Ser-Gly-Phe-Phe-Val-Phe) and smaller derivatives thereof were able to cause degranulation of human and rodent mast cells and thus might be useful in allergic desensitization therapy. (Biochem, J., 180, 665 (1979); Biochem, J., 181, 623 (1979); and European Patent Publication EP No. 0000252). No evidence was presented, however, that these peptides acted by virtue of binding to immunoglobulin Fc receptors.

VI. ATTEMPTS TO DISCOVER IgG, Fc RECEPTOR-BLOCKERS FOR NEUTROPHILS

Past attempts to isolate or synthesize peptides able to block IgG Fc receptors on Neutrophils have uniformly failed. Studies in which IgG was enzymatically degraded or otherwise chemically cleaved and resultant fragments tested for Fc receptor blocking activity demonstrated that no fragment smaller than an intact Fc fragment had measurable Fc receptor interaction. (Barnett-Foster, et al., J. Immunol, 120, 407 (1978); Barnett-Foster, et al., Mol. Immunol., 19, 407 (1982)).

VII. ATTEMPTS TO DISCOVER IgE, Fc RECEPTOR-BLOCKERS FOR MONOCYTE OR MACROPHAGES

Past attempts to isolate or synthesize peptides able to block IgE Fc receptors on monocytes/macrophages have uniformly failed. Studies in which IgE was enzymatically degraded or otherwise chemically cleaved and resultant fragments tested for Fc receptor blocking activity demonstrated that no fragment smaller than an intact Fc fragment had measurable IgE Fc receptor interaction. (Takatsu, et al., J. Immunol., 114, 1838 (1975); Dorrington, et al., Immunol. Rev., 41, 3 (1978); Perez-Montfort, et al., Mol. Immunol. 19, 1113 (1982)).

DETAILED DESCRIPTION OF THE INVENTION

This invention describes the sequences of new and useful peptides that can block the binding of human IgG immune complexes to IgG Fc receptors on human polymorphonuclear neutrophils (PMNs), of IgG and IgE immune complexes to IgG and IgE Fc receptors on monocytes and macrophages (MMs) and other white blood cells.

A further object is to describe how such new and useful peptides and their analogs and derivatives may be used to treat certain human diseases in which immune complexes contribute to disease pathogenesis. Such diseases include, but are not limited to, rheumatoid arthritis, systemic lupus erythematosus, glomerulonephritis, serum sickness, polyarteritis nodosa and other forms of vasculitis, and other diseases described under the generic category of "autoimmune diseases", idiopathic pulmonary fibrosis, hypersensitivity pneumonitis, asthma and other diseases and conditions.

A still further object is to describe how such peptides can prevent destruction of erythrocytes (red blood cells) and platelets (blood clotting cells) as occurs in certain autoimmune diseases such as autoimmune hemolytic anemias and idiopathic thrombocytopenic purpura, respectively.

A still further object is to describe how certain of these peptides bind to Fc receptors on other classes of white blood cells (lymphocytes and basophils) which enable such peptides to perform additional therapeutically useful functions.

Other objects and advantages of the invention will be apparent to those in the art from the preceding and following description of the invention.

PMNs AND MMs AS MEDIATORS OF IMMUNE COMPLEX-INDUCED INFLAMMATION

It is generally recognized that PMNs and MMs (monocytes are immature macrophages) accumulate in great numbers at the sites of most acute immunologically induced tissue injury. It has been recently appreciated that these cells are not mere passive "bystanders" in the inflammatory process, but rather directly contribute to tissue inflammation and destruction. PMNs contain cellular organelles known as lysosomes which contain proteolytic enzymes and inflammatory mediators sequestered in a latent, inactive form. Under certain conditions, PMNs and MMs are stimulated to release the contents of their lysosomes to the external cellular millieu, resulting in considerable tissue inflammation and cell death. Such inflammation and cell death are mediated by a variety of biologically active substances. The lysosomal granules of PMNs and MMs contain many different proteolytic and glycolytic enzymes (viz. collagenase which degrades collagen, elastase which degrades elastin, lysozyme which degrades certain types of carbohydrate polymers, etc.) which cause direct destruction of cartilage, connective tissue and cells. Certain of these enzymes may also activate the blood clotting system or inflammatory peptide mediators such as bradykinin or complement. Other important inflammatory mediators released by PMNs and MMs include prostaglandins (PGs) and leukotrienes (LTs) which have a variety of potent inflammatory and immunomodulatory effects. Some of these effects, together with the elicting substance are enumerated below.

(1) Prostaglandin E2 (PGE2)—PGE2 produces vasodialation, erythema, increased vascular permeability, edema (swelling), potentiates the inflammatory and pain producing actions of histamine and bradykinin and stimulates bacterial endotoxin-induced collagenase production by leukocytes. (Kuehl, et al., Science, 210, 978 (1980)).

PGE2 also has potent immunosuppressive effects and can suppress NK and ADCC-mediated killing of cancer cells, T cell colony growth, clonal proliferation of the committed granulocyte-macrophage stem cell and antigen and mitogen-induced B-lymphocyte maturation into antibody-secreting plasma cells. PGE2 also directly activates short-lived T suppressor lymphocytes which can, in turn, suppress other protective immune functions. Such PGE2-mediated suppression of the immune system is thought to be important in producing the immunosuppression that frequently accompanies various forms of cancer. (Goodwin, Clin. Immunol. Immunopath., 15, 106 (1980); Stenson, et al., Immunol. 125, 1 (1980); Oroller, et al., Cell. Immunol., 39, 165 (1978); Leung, et al., J. Immunol., 129, 1742 (1982); Fischer, et al., J. Immunol., 126, 1452 (1981); Klein, et al., Immunol., 48, 337 (1983); Goodwin, et al., Cancer Immunol. Immunother., 8, 3 (1980)).

(2) Leukotrienes C4 (LTC4), D4 (LTD4) and E4 (LTE4)—These leukotrienes, in various combinations, constitute the slow reacting substance of anaphylaxis (SRS-A) thought to be important in the pathogenesis of many inflammatory and allergic diseases, especially asthma. These leukotrienes are hundreds to thousands of times more potent, on a molar basis, than histamine in eliciting inflammation and pulmonary bronchoconstriction. (Samuelsson, Science, 220, 568 (1983)).

(3) Leukotriene B4 (LTB4)—This leukotriene is one of the most potent chemotatic substances known for certain human leukocytes. It is produced by preparations of human peripheral leukocytes, neutrophils, lung tissue and other cells. LTB4 attracts neutrophils, and eosinophils, both of which are present in high numbers at sites of inflammation.

LTB4 also stimulates the release of lysosomal enzymes, including lysozyme, from neutrophils which directly mediates tissue destruction. LTB4 is probably involved in the pathogenesis of many inflammatory conditions, including rheumatoid arthritis in which LTB4 is found in elevated concentrations in affected joints. (Samuelsson, Science, 220, 568 (1983); Science, 215, 1382 (1982)).

Immune complexes also cause PMNs and MMs to release highly reactive free radicals such as the superoxide anion ($O_2-$) which directly damages tissue which it contacts. (Weiss, et al., J. Immunol., 129, 309 (1982); Fantone, J. Pathol., 107, 397 (1982)).

Of particular importance to this invention is the fact that IgG and IgE containing immune complexes, aggregates or objects to which IgG or IgE is attached via Fab-mediated binding or by passive surface adsorption ("complexes") are potent stimulators of phagocytosis (engulfment and digestion of complexes, particulate matter and cells) by PMNs and MMs and subsequent enzyme and inflammatory mediator release. Such stimulation is known to depend on the binding of IgG or IgE Fc regions within immune complexes to Fc receptors located on the PMN or MM cell surface.

It is known that the exact molecular form in which Fc regions are presented to PMN Fc receptors (e.g., IgG or IgE antigen complexes, heat aggregated IgG or IgE, IgG or IgE passively adsorbed to cell or particulate surfaces) is not important in triggering lysosomal enzyme or inflammatory mediator release. The critical factor in common to these stimulatory forms of IgG or IgE is that multiple Fc regions in a fixed, relatively immobilized form be present to simultaneously bind to multiple PMN or MM Fc receptors. Such multiply engaged Fc receptors then trigger lysosomal enzyme or inflammatory mediator release.

EXAMPLES OF DISEASE PROCESSES IN WHICH IMMUNE COMPLEX-MEDIATED LYSOSOMAL ENZYME OR INFLAMMATORY MEDIATOR RELEASE CONTRIBUTE TO INFLAMMATION AND TISSUE DESTRUCTION

I. Rheumatoid Arthritis (RA)

Lesions of RA are thought to first develop within joint spaces. As as yet unidentified agent or condition triggers a local, intraarticular synthesis of IgG and IgM antibodies directed toward the Fc region of IgG. Such "rheumatoid factors (RFs)", being a type of immune complex, accumulate within the joint and bind to Fc receptors of leukocytes, including PMNs and of the complement system. Such binding triggers an initial inflammatory reaction which attracts blood-borne leukocytes, especially PMNs. PMNs in large numbers migrate into the joint space and, there, encounter RF immune complexes which trigger lysosomal enzyme secretion and subsequent cartilage and tissue destruction. While other leukocytes including monocytes and macrophages also contribute to the inflammation by a similar process, PMNs frequently constitue the great majority of cells present and often exceed 25,000 PMNs per cubic millimeter. RFs also activate the complement system which, in conjunction with PMNs and other cells and molecules, produce the tissue destruction characteristic of the disease. (Perez, et al. in Textbook of Rheumatology, Vol. 1 (W. B. Saunders: Philadelphia, 1981), pp. 179–194.) Some of the peptides detailed in the present invention can block IgG immune complex binding to PMNs, monocytes and macrophages and can thereby reduce or prevent inflammation and tissue destruction of rheumatoid arthritis and other immune complex-mediated inflammation.

II. Idiopathic Pulmonary Fibrosis

Idiopathic Pulmonary Fibrosis (IPF) is a condition in which the normally thin, gas permeable wall of the lung's respiratory unit, the alveolus, is greatly thickened and replaced with large amounts of relatively gas-impermeable, fibrous connective tissue. This greatly reduces the lung's ability to respire and may lead to chronic pulmonary incapacitation and death. IPF frequently accompanies idiopathic interstitial pneumonias and the interstitial pneumonias of rheumatoid arthritis, systemic lupus erythematosus, scleroderma and polymyositis-dermatomyositis. (Dreisin, et al., N. Engl. J. Med. 298, 353 (1978)). The final common pathway leading to the tissue destruction in IPF is believed to involve IgG-immune complexes produced either systemically or locally within the lung parenchyma. (Lawrence, et al., N. Engl. J. Med. 302, 1187 (1980)). Localization of immune complexes within the lung leads to an influx of PMNs and monocytes from blood which accumulate in large numbers within the interstitium and within alveolar structures. Monocytes then develop into mature macrophages and join the normally present pulmonary macrophages. IgG Fc regions within the immune complexes then combine with PMN and MM Fc receptors causing lysosomal enzyme and inflammatory mediator release, inflammation and alveolar destruction. (Hunninghake, et al., Clin. Immunol. Rev., 1 (3), 337 (1981–1982)). Over a period of time, this process results in "scarring" and generalized pulmonary fibrosis. Some of the peptides detailed in the present invention can block IgG-immune complex binding to IgG Fc receptors on PMNs, monocytes and macrophages and can thereby reduce or prevent inflammation and tissue destruction of idiopathic pulmonary fibrosis and other immune complex-mediated diseases.

III. Immune Complex-Induced Glomerulonephritis

The glomeruli of kidneys are the filtration devices which separate from blood the plasma ultrafiltrate that ultimately becomes urine. Glomeruli are easily damaged by the inflammatory processes initiated by immune complexes which accumulate as a result of the blood filtration process. At an early stage of immune complex-induced glomerular injury, monocytes and macrophages accumulate in the glomerular mesangium where they encounter immune complexes. IgG Fc regions within these complexes bind to IgG Fc receptors of the monocytes and macrophages and are thereby stimulated to release lysosomal enzymes and the inflammatory mediators previously discussed. These substances produce glomerular inflammation, (glomerulonephritis) which may lead to kidney failure and subsequent death. (Holdsworth, J. Immunol., 130, 735 (1983); Striker, J. Exp. Med. 149, 127 (1979); Hunsicker, J. Exp. Med., 150, 413 (1979)). Immune complex-mediated glomerulonephritis and resultant kidney failure, for example, is the single leading cause of death in patients with systemic lupus erythematosis. (Kumar in Pathologic Basis of Disease, eds. S. L. Robbins and R. S. Cotran (W. B. Saunders: Philadelphia, 1979), p. 304.) Many other conditions such as rheumatoid arthritis, other autoimmune diseases, infectious diseases such as streptococoal or hepatitis virus infection and others are accompanied by glomerulonephritis caused by immune complexes. Some of the peptides detailed in the present invention can block IgG immune complex binding to monocyte and macrophage IgG Fc receptors and can thereby reduce or prevent inflammation and tissue destruction of immune complex-mediated glomerulonephritis.

IV. Immune Complex Mediated Lung-Inflammation of Hypersensitivity Pneumonitis Hypersensitivity Pneumonitis (HP) includes a spectrum of conditions characterized by granulomatous interstitial and alveolar-filling lung diseases associated with exposure to a wide range of inhaled organic dusts and particles. Affected individuals synthesize relatively large amounts of IgG directed against the offending inhaled dust and produce IgG immune complexes within the lung parenchyma. These complexes bind to IgG Fc receptors of PMNs, monocytes and pulmonary macrophages which, in a manner similar to that previously discussed, are stimulated to release lysosomal enzymes and inflammatory mediators which produce an acute pneumonia. If this process is continued for a period of time, the lung damage may become permanent in the form of chronic granulomatous interstitial pneumonitis. (Stankus, Allergologie, 4, 8 (1981)). Some of the peptides detailed in the present invention can block IgG-immune complex binding to IgG Fc receptors of PMNs, monocytes and macrophages and can thereby reduce or prevent inflammation and tissue destruction of hypersensitivity pneumonitis and other immune-complex mediated diseases.

V. IgE-Immune Complex-Mediated Inflammation to Asthma

Atopic (IgE-mediated) asthma is an inflammatory lung disease in which IgE bound to pulmonary mast cells and circulating basophil Fc receptors causes them to release inflammatory mediators upon exposure to the sensitizing allergan (antigen). It is also known that IgE not already bound to cellular Fc receptors may also bind to the sensitizing allergan to form IgE-allergan immune complexes. There circulating IgE immune complexes may then bind to monocyte or macrophage IgE Fc receptors causing them to release the various inflammatory mediators previously discussed. Additionally, IgG directed against the sensitizing allergan may be present and may also produce IgG-allergan immune complexes. These complexes may then bind to IgG Fc receptors on PMNs and monocytes and macrophages in the lungs and thereby contribute to lysosomal enzyme and inflammatory mediator release. Some of the peptides detailed in the present invention can block IgE-immune complex binding to IgE Fc receptors on monocytes and macrophages and can thereby reduce or prevent inflammation characteristic of asthma and other disease pathogenesis. (Melewicz, et al., Clin. Exp. Immunol., 49, 364 (1982); Spiegelberg, et al., 42, 124 (1983); Scott, et al., Fed. Proc., 42, 129 (1983)).

EXAMPLES OF OTHER IMMUNE DISEASES

I. Autoimmune Hemolytic Anemias

This autoimmune disease arises when certain immune system cells recognize antigens on erythrocytes (red blood cells) as foreign and cause the synthesis of antibodies (usually IgG) directed toward the erythrocytes. This "anti-erythrocyte Ig" then binds to the erythrocyte via its Fab antigen-binding arms, leaving the Fc region exposed to the erythrocyte exterior. Macrophages, and to a lesser extent monocytes then bind to such IgG-sensitized erythrocytes via cell surface IgG Fc receptors. Most such binding occurs in the spleen and results in phagocytosis and destruction of erythrocytes and subsequent anemia.

Some of the peptides detailed in the present invention can block IgG receptors on monocytes and macrophages and can therefore reduce or prevent IgG Fc-mediated destruction of erythrocytes and subsequent anemia. (Engelfriet, et al. in A Seminar on Immunemediated cell destruction (American Association of Blood Banks: Washington, D.C.), pp. 93–130 (1981).

II. Idiopathic (Autoimmune) Thrombocytopenic Purpura (ITP)

ITP is a syndrome characterized by chronic thrombocytopenia (low platelet count) caused by a circulating antiplatelet antibody that results in platelet destruction by phagocytic leukocytes. In most patients, the antibody is of the IgG class and is directed toward a normally present platelet-associated antigen. When IgG-coated platelets encounter macrophages and monocytes, especially in the spleen, the exposed IgG Fc regions on the platelets bind to IgG Fc receptors on macrophages and monocytes and stimulate platelet phagocytosis and destruction. (McMillian, N. Engl. J. Med., 304, 1135 (1981)). Agents which block macrophage and monocyte IgG Fc receptors are known to be efficacious in treating this condition. For example, Fehr, et al. (N. Engl. J. Med., 306, 1254 (1982)) and Imbach, et al. (Lancet, June 6, 1981, p. 1228) demonstrated that intervenous, monomeric IgG administered to patients with ITP significantly reduced platelet destruction. They attributed the observed efficacy to blockade of IgG Fc receptors of macrophages and other phagocytic leukocytes. Some of the peptides detailed in the present invention can block macrophage and monocyte IgG Fc receptors and thus represent a significant improvement over intervenous IgG since peptides are relatively inexpensive to produce and do not carry with them the risk of infectious disease transmission (e.g., hepatitis) which accompanies human blood products.

PEPTIDES WHICH BLOCK IMMUNE COMPLEX BINDING TO Fc RECEPTORS MAY ALSO ACT AS IMMUNOSTIMULANTS

In addition reducing or preventing immune-complex-mediated inflammation and tissue destruction, the peptides disclosed in this invention may have either important effects on the immune system which may prove to be therapeutically efficacious in treating human diseases.

As described earlier in this disclosure, when IgG complexes bind to monocyte IgG Fc receptors, monocytes secrete prostaglandin E2 (PGE2) which inhibits many important immune defense functions. These inhibited functions include Natural Killer (NK) cell and ADCC killing of cancer cells, growth and development of T lymphocytes, and granulocyte-macrophage stem cells and antigen and mitogen-induced B-lymphocyte maturation into protective antibody-secreting plasma cells. Additionally, PGE 2 also directly activates short-lived suppressor lymphocytes which may in turn, suppress other protective immune functions. The peptides described in this invention which block IgG immune complexes to monocyte IgG Fc receptors may, therefore be expected to act as immunostimulants by virtue of their ability to inhibit immune complex-mediated PGE 2 secretion.

Some of the peptides described in the present invention also demonstrate the ability to block IgG and/or IgE immune complex binding to lymphocyte Fc receptors. Such abilities may be expected to be therapeutically useful in several ways.

I. Immunostimulation

All antibodies are synthesized by plasma cells which develop from B lymphocytes. B lymphocyte-to-plasma cell development is, therefore, critical for the production of protective antibody synthesis. Substances which inhibit this development may result in an inadequate concentration of antibodies and may render a person susceptible to infection. Of particular importance to the present invention is the fact that complexes or aggregates of antigen and antibody, termed immune complexes, are potent inhibitors of B lymphocyte development. Such inhibition is thought to occur by several mechanisms, all of which require that Fc regions of antibodies within the immune complex bind to lymphocyte Fc receptors.

Figure 3:
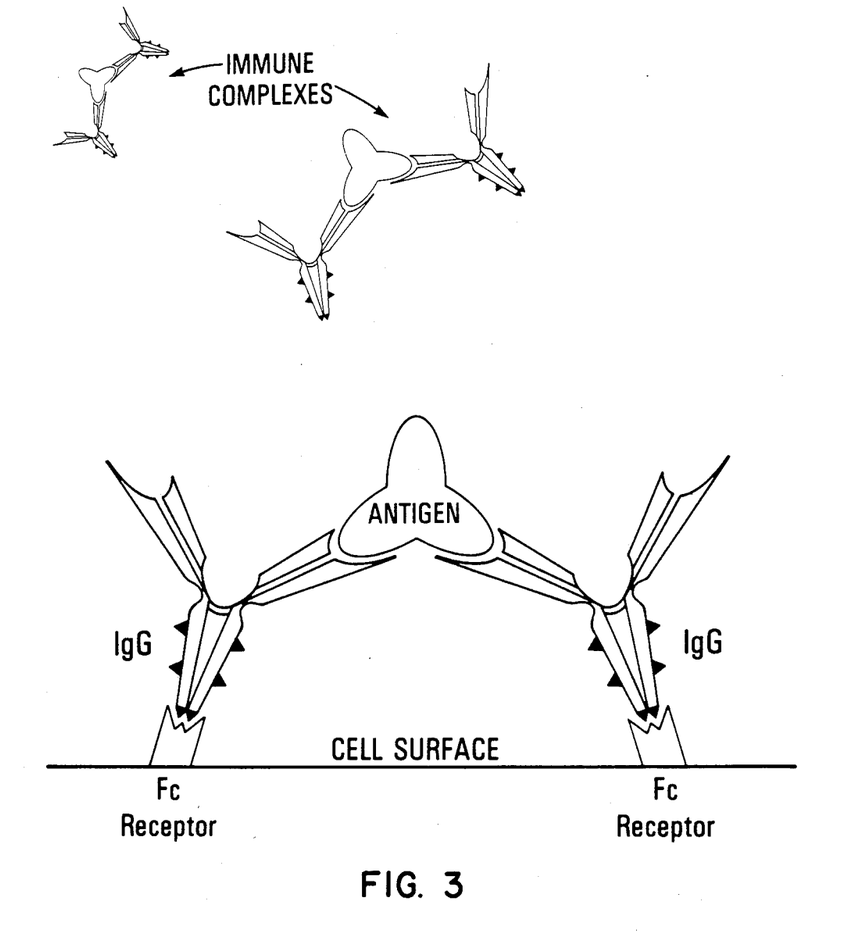
FIG. 3 is a schematic illustrating an immune complex bound, via its Fc region active sites, to two cellular Fc receptors.
Figure 4:
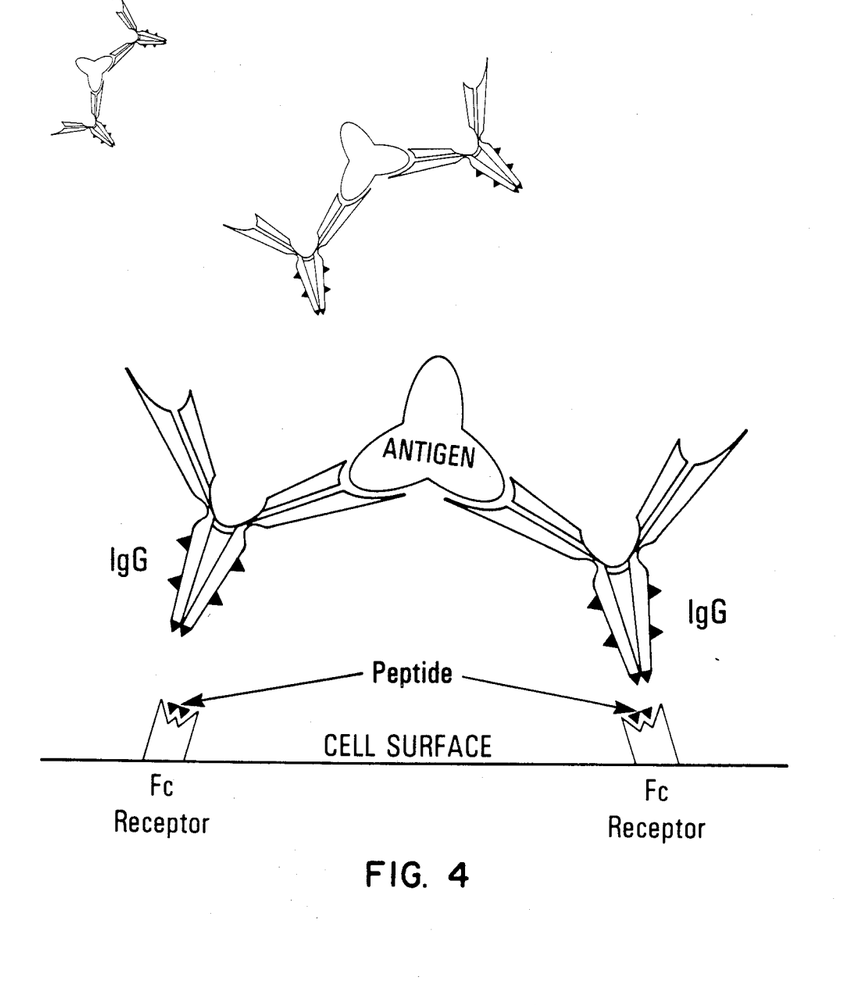
FIG. 4 is a schematic illustrating active site peptides which bind to and block cellular Fc receptors, thus preventing the immune complex's immunological activity. Such Fc receptor blockage forms the basis of the present invention.

One well characterized mechanism of immune complex-induced B-lymphocyte suppression occurs when IgG Fc regions within an immune complex bind to IgG Fc receptors on B lymphocytes. Because such an immune complex contains two or more IgG Fc regions, two or more Fc receptors may be simultaneously bound and thus "crosslinked" by virtue of the antigen-antibody bridge (FIG. 3). It is believed that this crosslinking of Fc receptors directly triggers the B lymphocyte inhibition (Oberbarnscheidt, et al., Immunol., 35, 151 (1978); Kolsch, et al., Immunol. Rev., 49, 61 (1980)). Some of the peptides detailed in the present invention can bind to B lymphocyte Fc receptors and thus prevent immune complexes from binding. Because peptides do not cause Fc receptor crosslinking, they can prevent immune complex-mediated inhibition of B lymphocyte development (FIG. 4). The clinical effect of such a peptide would be to cause stimulation of protective antibody synthesis.

Another mechanism whereby IgG or IgE Fc receptor-blocking peptides may stimulate antibody synthesis involves immunoglobulin-binding factors (IBFs). IBFs are soluble Fc receptors released from activated T lymphocytes, PMNs and possibly monocytes and macrophages. IgG IBF is a potent suppressor of B lymphocyte development into antibody-secreting plasma cells.

In order to produce such suppression, it is believed that IgG IBF must first bind to Fc regions of IgG molecules and to molecular structures on the surface of B lymphocytes. It is known that IgG IBF-mediated suppression is abrogated if IBF is prevented from binding to IgG Fc regions. (Fridman, et al., Immunol. Rev., 56, 51 (1981); Bich-Thuy, J. Immunol., 129, 150 (1982)). It is therefore expected that peptides which bind to and thus block IBF Fc receptors should also block IBF-mediated B lymphocyte suppression. These peptides should cause stimulation of protective antibody synthesis.

A third mechanism whereby peptides of the present invention may stimulate responsiveness involves peptide modulation of a substance known as T cell Replacing Factor (TRF). TRF is secreted by certain T lymphocytes ("helper T cells") under activating conditions such as exposure to antigen or artificial mitogens. TRF then binds to receptors on B lymphocytes which, in turn, triggers development into plasma cells. There is considerable evidence that the TRF receptor also binds to IgG Fc regions and therefore is also an Fc receptor. TRF is believed to stimulate B lymphoctye development by binding to the TRF/Fc receptor and thus preventing IgG immune complexes from binding to the same receptor. By this mechanism. TRF directly stimulates B lymphocyte development and prevents immune complexes from inhibiting development. (Kolsch, et al., Immunol. Rev., 49, 35 (1980)). Some of the peptides described in the present disclosure can, like TRF, bind to B lymphocyte Fc receptors and are therefore expected to share some of TRFs immunostimulatory activities.

II. Immunomodulation

Interactions between the various leukocytes which constitute the cellular arm of the immune system are necessary for normal immune function. The induction of most immune responses is triggered by interactions between T lymphocytes and antigen-presenting cells. During this process, different subsets of T lymphocytes proliferate and differentiate into functionally distinct cells with helper, suppressor, inducer or killer activities. These cells may then, in turn, directly participate in immune defense or may activate the defensive functions of other leukocytes such as B lymphocytes or monocytes/macrophages.

An in vitro counterpart of these in vivo events is the autologous mixed lymphocyte reaction (AMLR). In the AMLR, normal T lymphocytes are stimulated to proliferate when co-cultured with autologous non-T lymphocytes including monocytes/macrophages and B lymphoctyes. This reaction is thought to approximate many of the cellular processes that occur during a normal immune response. (Smolen, et al., J. Immunol., 129, 1050 (1982); Goeken, et al., Hum. Immunol., 6, 79 (1983)).

Of particular importance to the present invention is the fact that IgG immune complexes are potent inhibitors of the AMLR. Immune complexes are thought to directly exert their inhibitory effects on T lymphocytes by binding to IgG Fc receptors of the T lymphocytes which normally participate in the AMLR reaction. (Kabelitz, et al., Eur. J. Immunol., 12, 687 (1982)).

The AMLR is greatly suppressed in patients with a variety of autoimmune or neoplastic diseases including systemic lupus erythematosus (Sakane, et al., Proc. Natl. Acad. Sci. U.S.A., 75, 3464 (1978)). Sjögren's syndrome (Miyasaka, et al., J. Clin, Invest., 66, 928 (1980)), primary biliary cirrhosis (James, et al., J. Clin. Invest., 66, 1305 (1980)), Hodgkin's lymphoma (Engleman, et al., J. Clin. Invest., 66, 149 (1980)), and chronic lymphocytic leukemia (Smith, et al., J. Natl. Cancer Inst., 58, 579 (1977)). This suppression is thought to be due, in part, to the inhibitory effects of IgG immune complexes on normal T lymphocyte function. Some of the peptides disclosed in the present invention can block IgG immune complex binding to T lymphocytes and can therefore block immune-complex-induced inhibition which is thought to be important in the pathogenesis of the above conditions.

Peptides which block immune complex binding to Fc receptors may also be expected to stimulate cellular or delayed type hypersensitivity (DTH) which is known to be important in defense against cancer and certain infectious diseases such as tuberculosis. Immune complexes can significantly inhibit DTH in experiments using mice (Douvas, Ann. Immunol. Inst. Pasteur, 132C, 307 (1981)). Such inhibition is known to be dependent on the presence of Fc regions within the immune complex which bind to cellular Fc receptors.

III. Immunoinhibition

Antibody-dependent cell-mediated cytotoxity (ADCC) is a process by which T lymphocytes, monocytes/macrophages and polymorphonuclear neutrophils destroy foreign or infectious cells. IgG antibodies must first bind to antigens on the target cell which sensitizes the cell for recognition by ADCC cells. Upon encounter wih an IgG-sensitized target, IgG Fc receptors on the ADCC cell bind to exposed Fc regions on the surface of the target cell. Such Fc receptor binding activates the ADCC cell to directly lyse the target cell, causing its death.

Inappropriate cell killing via ADCC is thought to mediate some of the inflammation and organ destruction which occurs in chronic active hepatitis (Cochrane, et al., Lancet, 1, 441 (1976)). Ulcerative colitis (Hibi, et al., Clin. Exp. Immunol., 49, 75 (1982)). Hashimoto's thyroiditis (Calder, et al., Clin. Exp. Immunol., 14, 153 (1973)), and other conditions. Some of the peptides disclosed in the present invention can block lymphocyte IgG Fc receptors and are therefore useful to block ADCC-mediated killing. Such inhibition is expected to prevent much of the inflammation and tissue destruction characteristic of the above diseases.

PEPTIDES WHICH EXERT A DIRECT ANTI-ALLERGIC EFFECT

Certain of the peptides described in this invention have antiallergic activities, in addition to the effects previously described. It is known that IgE-mediated allergies (viz. allergic rhinitis (hayfever), types of asthma, allergic reactions to insect stings) occur by a mechanism in which IgE is bound, via its Fc region, to IgE Fc receptors located on mast cells and basophils. When the offending allergan (the antigen which originally elicited IgE synthesis) is presented to such sensitized mast cells and basophils and binds to the cell-bound IgE, inflammatory mediators are released which produce the immediate allergic reaction characteristic of allergies. If the sensitizing IgE is prevented from binding to mast cell or basophil IgE Fc receptors, however, mediator release does not occur. It is known that mast cell and basophil IgE Fc receptors may be blocked by administering either chemically isolated IgE Fc fragments or certain peptides that are described in the United States and foreign patents discussed above. Such compounds have affinity for the IgE Fc receptor and thus bind to it and prevent IgE from binding. In this manner, the allergic response can be abrogated independent of the particular antigen which elicited IgE synthesis. (Hamburger, *Science,* 189, 389 (1975); Hamburger, Adv. Allergology Immunol. (Pergamon Press: New York, 1980), pp. 591–593; Plummer, et al., Fed. Proc., 42, 713 (1983)).

Certain of the peptides described in the present invention can bind to IgE Fc receptors on human basophils and can block subsequent IgE binding. These peptides therefore have antiallergic properties which may be useful in the treatment of allergy in animals and in humans.

ACTIVE SITE PEPTIDES OF THE INVENTION

As indicated above, this invention is concerned with a method of blocking immune-complex-mediated inflammation, new peptides having therapeutic value in various areas, therapeutic compositions containing these peptides, and methods for use thereof.

The present invention provides active site peptides having the following sequence:

Arg-Ser-Thr-Thr-Lys-Thr-Ser-Gly-Pro-Arg.

It is to be considered that the scope of the present invention is inclusive of the unsubstituted peptides as well as those which are terminally substituted by one or more functional groups which do not substantially affect the biological activity disclosed herein. From this statement it will be understood that these functional groups include such normal substitution as acylation on the free amino group and amidation on the free carboxylic acid group, as well as the substitution of amino acids such as the D-isomers of the naturally occurring amino acids. The peptides of this invention are highly unusual since they are able to bind to and block cellular Fc receptors in the same manner as the much larger parent IgG or IgE molecules, a portion of which they resemble. It is especially unusual and surprising that some of these peptides can bind to and block (i) IgG receptors of PMNs; (ii) IgG and IgE receptors of lymphocytes; and (iii) IgE receptors of monocytes since scientific investigators skilled in the art described herein have concluded in the recent scientific literature that appreciable Fc receptor binding, as described in examples 1–3, requires, at minimum, an intact Fc region of the IgC and IgE molecules. (Barnett-Foster, et al., Mol. Immunol., 19, 407 (1982) Barnett-Foster, et al., J. Immunol., 120, 407 (1978), Perez-Montfort, et al., Mol. Immunol., 19, 1113 (1982), Dorrington, et al., Immunol. Re., 41, 3 (1978); Takatsu, et al., J. Immunol., 114, 1838 (1975); Seiler, et al., Immunobiol., 158, 254 (1981)).

It is believed therefore that the activity requirements of the molecules are dictated by each molecule's sterochemistry, that is, the particular "folding" of the molecule. In this regard, it should be understood that polypeptide bonds are not rigid but flexible, thus allowing polypeptides to exist as sheets, helices, and the like. As a result, the molecules are flexible and will "fold" in a certain way. In the present invention it has been discovered that the peptides "fold" in the same manner as the long chain parent polypeptide and therefore exhibit the same biological characteristics. For this reason, the peptides may be substituted by various functional groups so long as the substituents do not substantially affect the biological activity or interfere with the natural "folds" of the molecule.

The ability of the peptides to retain their biological activity and natural folding is illustrated by the fact that they have Fc receptor binding activity similar to the parent antibody molecules. While the peptides of the present invention are believed to act by "blocking" Fc receptor activity as described herein, it is not intended that the present invention be limited to any particular mechanism of action.

The Fc receptor blocking activity of the subject peptides was assessed using well established techniques and procedures. In particular, a rosette assay was employed which uses either monomeric, chemically or heat aggregated human IgG or IgE obtained from human myeloma sera. (Gonzalez-Molina, et al., J. Clin. Invest., 59, 616 (1977); Spiegelberg, et al. in Immunoassays: Clinical Laboratory Techniques for the 1980's (Alan R. Liss: New York, 1980), pp. 287–300). The IgG or IgE is then adsorbed to ox-erythrocytes which has been previously treated with trypsin and pyruvic aldehyde. Fresh human cell PMNs, monocytes and basophils from a patient with basophilic chronic myelogenous leukemia or human cell lines (RPMI-8866, and Daudi for lymphocyte Fc receptors and U937 for monocyte/macrophage Fc receptors) were then incubated in the presence or absence of inhibitors (monomeric IgG or IgE or peptides) at equal concentrations for fifteen minutes before addition of the indicator oxerythrocytes. In the absence of inhibitors, the cells expresing surface Fc receptors formed rosettes, clusters of three or more indicator erythrocytes that bound to the cells by virtue of exposed Fc regions on the erythrocyte surface. Addition of inhibitor myeloma proteins or inhibitor peptides produced a reproducable reduction of rosette formation, calculated by dividing the percentage of rosettes formed when the diluent, phosphate buffered isotonic saline, was used alone as control and then multiplying the calculated quotient by 100.

Table 1 presents the inhibition observed by representative peptide inhibitors calculated as a percentage of the inhibition observed with intact, monomeric myeloma proteins. Thus, 50 percent inhibition implys that the peptide was 50% as inhibitory as the intact myeloma protein to which it was compared.

TABLE 1

ROSETTE INHIBITION EXPRESSED AS PERCENT INHIBITION BY MONOMERIC IgG or IgE

| PEPTIDE | NEUTROPHIL (PMN) Fc Receptor IgG | MONOCYTE/ MACROPHAGE Fc Receptor IgG | MONOCYTE/ MACROPHAGE Fc Receptor IgE | LYMPHOCYTE Fc Receptor IgG | LYMPHOCYTE Fc Receptor IgE | BASOPHIL Fc Receptor IgG | BASOPHIL Fc Receptor IgE |
|---|---|---|---|---|---|---|---|
| Thr—Val—Leu—His—Gln—Asn—Trp—Leu—Asp—Gly—Lys | 88 | 74 | 95 | 34 | 95 | 78 | 100 |
| Ac—Gln—Pro—Glu—Asn | 95 | 19 | 55 | 94 | NS | 74 | 89 |
| Pro—Asp—Ala—Arg—His—Ser | 95 | 100 | 87 | 95 | 98 | 105 | 101 |
| Thr—Thr—Gln—Pro—Arg | NS | NS | 58 | 36 | NS | NS | 80 |
| Pro—Asp—Ala—Arg—His—Ser—Thr—Thr—Gln—Pro—Arg | 241 | 103 | 103 | 92 | 100 | ~120 | ~130 |
| Thr—Ile—Ser—Lys—Ala—Lys—Gly—Gln—Pro—Arg | 124 | 100 | 87 | 84 | 106 | 108 | 133 |

NS indicates inhibition not significantly different from 0

TABLE 2

| TREATMENT | CONCENTRATION μg/ml | COUNTS/MINUTE NO PEPTIDE | COUNTS/MINUTE PEPTIDE (100 μg/ml) | PEPTIDE INHIBITION |
|---|---|---|---|---|
| Culture medium only | — | 228 | 343 | −50 |
| Concanavalin A | 6.25 | 724 | 338 | 53 |
| Concanavalin A (Succinylated) | 100. | 5624 | 2989 | 47 |
| Phytohemagglutinin | 6.25 | 3664 | 1897 | 48 |
| Polkweed mitogen | 0.05 | 2427 | 1413 | 42 |
| Lens culinaris agglutinin | 25. | 5460 | 2391 | 56 |
| Vicia faba agglutinin | 12.50 | 2200 | 1669 | 24 |

Legend:
Effect of Thr—Ile—Ser—Lys—Ala—Lys—Gly—Gln—Pro—Arg on spontaneous and lectin-induced mitogenesis of human peripheral mononuclear cells. Numbers shown are counts per minutes from $^{125}$I-Iododeoxyuridine incorporation on day three of culture.

TABLE 3

ROSETTE INHIBITION EXPRESSED AS PERCENT INHIBITION BY MONOMERIC IgG or IgE

| PEPTIDE | LYMPHOCYTE Fc Receptor IgG | LYMPHOCYTE Fc Receptor IgE | MONOCYTE/ MACROPHAGE Fc Receptor IgG | MONOCYTE/ MACROPHAGE Fc Receptor IgE | NEUTROPHIL (PMN) Fc Receptor IgG | BASOPHIL Fc Receptor IgG | BASOPHIL Fc Receptor IgE |
|---|---|---|---|---|---|---|---|
| Arg—Ser—Thr—Thr—Lys—Thr—Ser—Gly—Pro—Arg | 100 | 87 | 75 | 87 | NS | 90 | 110 |
| Tyr—Ser—Lys—Leu—Thr—Val—Asp—Lys—Ser—Arg | 29 | NS | NS | 33 | NS | NS | 89 |
| Asp—Lys—Ser—Arg | 86 | 23 | 49 | 38 | 27 | 64 | 89 |
| Asp—Lys—Ser—Arg—Ala—Gln—Gln—Gly—Asn | NS | NS | NS | NS | NS | NS | 74 |
| Asp—Lys—Ser—Lys | 16 | NS | NS | NS | NS | NS | 94 |

NS indicates inhibition not significantly different from 0

TABLE 4

ROSETTE INHIBITION EXPRESSED AS PERCENT INHIBITION BY MONOMERIC IgG or IgE

| PEPTIDE | BASOPHIL Fc Receptor IgE | BASOPHIL Fc Receptor IgG | NEUTROPHIL (PMN) Fc Receptor IgG | MONOCYTE/ MACROPHAGE Fc Receptor IgG | MONOCYTE/ MACROPHAGE Fc Receptor IgE | LYMPHOCYTE Fc Receptor IgG | LYMPHOCYTE Fc Receptor IgE |
|---|---|---|---|---|---|---|---|
| Thr—Arg—Ala—Glu—Ala—Glu—Gln—Lys—Asp | 108 | NS | NS | NS | 21 | NS | NS |
| Thr—Arg—Ala—Glu | 41 | 44 | NS | 24 | 20 | 49 | NS |
| Glu—Gln—Lys—Asp | 106 | 18 | NS | NS | NS | NS | NS |
| Ser—Val—Met—His—Glu—Ala—Leu—His—Asn—His—Tyr—Thr—Gln—Lys | 74 | NS | NS | NS | 28 | NS | NS |
| Asp—Ser—Asn—Pro—Arg | 37 | NS | NS | NS | 48 | NS | NS |

NS indicates inhibition not significantly different from 0

Table 2 demonstrates representative immunostimulatory and immunomodulatory activity of one of the subject peptides, viz. Thr-Ile-Ser-Lys-Ala-Lys-Gly-Gln-Pro-Arg when incubated with normal human mononuclear cells (lymphocytes and monocytes) separated by ficoll-metronidizole gradient. The cells were exposed to the peptide (final peptide concentration = 100 micrograms/ml) followed by addition of various plant-derived lectins (mitogens) which have well characterized immunomodulatory activity. Mitogenic lectins are thought to mimic some of the cellular events that accompany antigenic stimulation of leukocytes and are useful indicators of cellular immune reactivity, in vitro. Following lectin addition, the cells were cultured for several days and, at specified intervals, "pulsed" with radioactive Iododeoxyuridine which becomes incorporated into newly synthesized DNA of dividing cells.

After the cells were harvested and washed, the amount remaining cell-associated radioactivity may be used to estimate the degree to which the cells were stimulated to proliferate. Table 2 shows that the peptide strongly inhibited the mitogenic effects of the six mitogens indicating that the peptide can substantially modulate the proliferative ability of immunologically important mononuclear cells and thus has use as an immunomodulator. The peptide alone also stimulated mitogenesis (proliferation) of mononuclear cells by 50% on day 3, 331% on day 5 and 283% on day 7. This indicates that the peptide can act as an immunostimulant by enhancing proliferation of mononuclear cells.

In the practice of the method of the present invention, an effective amount of a polypeptide or derivative thereof, or a pharmaceutical composition containing same, as defined above, is administered via any of the usual and acceptable methods known in the art, either singly or in combination with another compound or compounds of the present invention or other pharmaceutical agents such as antihistamines, corticosteriods, and the like. These compounds or compositions can thus be administered orally, sublingually, topically (e.g. on the skin or in the eyes), parenterally (e.g., intramuscularly, intravenously, subcutaneously or intradermally), or by inhalation, and in the form of either solid, liquid or gaseous dosage including tablets, suspensions, and aerosols, as discussed in more detail hereinafter. The administration can be conducted in single unit dosage form with continuous therapy or in single dose therapy ad libitum.

In one preferred embodiment, the method of the present invention is practiced when the relief of symptoms is specifically required or perhaps imminent; in another preferred embodiment, the method hereof is effectively practiced as continuous or prophylactic treatment.

In view of the foregoing as well as in consideration of the degree of severity of the condition being treated, age of subject, and so forth, all of which factors being determinable by routine experimentation by one skilled in the art, the effective dosage in accordance herewith can vary over a wide range. Since individual subjects vary in their Fc receptor content, an effective systemic dosage in accordance herewith can best be described as between $2 \times 10^3$ and $2 \times 10^6$ times the Fc receptor content, on a molar scale. For an averge subject this would be between about 0.5 and 500 mg/kg/day, depending upon the potency of the compound. Of course, for localized treatment, e.g., of the respiratory system, proportionately less material will be required.

Useful pharmaceutical carriers for the preparation of the compositions hereof, can be solids, liquids or gases; thus, the compositions can take the form of tablets, pills, capsules, powders, enterically coated or other protected formulations (such as by binding on ion exchange resins or other carriers, or packaging in lipid-protein vesicles or adding additional terminal amino acids or replacing a terminal amino acid in the L-form with one in the D-form), sustained release formulations, solutions (e.g., opthalmic drops), suspensions, elixirs, aerosols, and the like. The carrier can be selected from the various oils including those of petroleum, animal, vegetable or synthetic origin, for example, peanut oil, soybean oil, mineral oil, sesame oil, and the like. Water, saline, aqueous dextrose, and glycols are preferred liquid carriers, particularly (when isotonic) for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulation are described in "Remington's Pharmaceutical Sciences" by E. W. Martin. Such compositions will, in any event, contain an effective amount of the active compound together with a suitable amount of carrier so as to prepare the proper dosage form for proper administration to the host.

To be effective for the prevention or treatment of the allergic reaction it is important that the therapeutic agents be relatively non-toxic, non-antigenic and non-irritating at the levels in actual use.

SYNTHESIS OF PEPTIDES

Peptides of this invention were synthesized by the solid phase peptide synthesis (or Merrifield) method. This established and widely used method, is described, including the experimental procedures, in the following references:

Merrifield, J. Am. Chem. Soc., 85, 2149–2154 (1963).
Meinehofer in "Hormonal Proteins and Peptides," ed. C. H. Li, Vol. 2 (Academic Press, 1973), pp. 48–267.
Barany and Merrifield in "The Peptides," eds. E. Gross and F. Meinenhofer, Vol. 2 (Adademic Press, 1980), pp. 3–285.

A preferred method for synthesizing the peptides of the present invention is the so-called "Merrifield" synthesis technique which is well known to those skilled in the art and is set forth in detail in the article entitled "Synthesis of a Tetrapeptide" by R. B. Merrifield, Journal of the American Chemical Society (Vol. 85, pp. 2149–2154 (1963)) as well as Meinehofer, cited above.

In this preferred method a peptide of any desired length and of any desired sequence is produced through the stepwise addition of amino acids to a growing peptide chain which is bound by a covalent bond to a solid resin particle.

In the preferred application of this method the C-terminal end of the growing peptide chain is covalently bound to a resin particle and amino acids having protected amino groups are added in the stepwise manner indicated above. A preferred amino protecting group is the t-BOC group, which is stable to the condensation conditions and yet is readily removable without destruction of the peptide bonds or racemization of chiral centers in the peptide chain. At the end of the procedure the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acid conditions.

The cleaved peptides are isolated and purified by means well known in the art such as, for example, lyophilization followed by either exclusion or partition chromatography on polysaccharide gel media such as Sephadex G25, or countercurrent distribution. The composition of the final peptide may be confirmed by amino acid analysis after degradation of the peptide by standard means.

Salts of carboxyl groups of the peptide may be prepared in the usual manner by contacting the peptide, with one or more equivalents of a desired base such as for example, a metallic hydroxide base, e.g., sodium hydroxide; a metal carbonate or bicarbonate base such as for example sodium carbonate or sodium bicarbonate; or an amine base such as for example triethylamine, triethanolamine, and the like.

Acid addition salts of the polypeptides may be prepared by contacting the polypeptide with one or more equivalents of the desired inorganic or organic acid, such as, for example, hydrochloric acid.

Esters of carboxyl groups of the polypeptides may be prepared by any of the usual means known in the art for converting a carboxylic acid or precursor to an ester. One preferred method for preparing esters of the present polypeptides, when using the Merrifield synthesis technique described above, is the cleave the completed polypeptide from the resin in the presence of the desired alcohol either under basic or acidic conditions, depending upon the resin. Thus the C-terminal end of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin Either acylation may be carried out using standard acylating reagents such as acyl halides, anhydrides, acyl imidazoles, and the like. Both N- and O-acylation may be carried out together, if desired.

The coupling, deprotection/cleavage reactions and preparation of derivatives of the subject polypeptides are suitably carried out at temperatures between about $-10°$ and $+50°$ C., most preferably about $20°-25°$ C. The exact temperature for any particular reaction will of course be dependent upon the substrates, reagents, solvents and so forth, all being well within the skill of the practitioner. Illustrative reaction conditions for these processes may be gleaned from the examples.

The following examples are given to enable those skilled in the art to more fully understand and practice the present invention. They should not be construed as a limitation upon the scope of the invention, but merely as being illustrative and representative thereof.

EXAMPLE 1

Preparation of the 11-peptide (or undecapeptide)
Thr-Val-Leu-His-Gln-Asn-Trp-Leu-Asp-Gly-Lys 5.3 g α-t-BOC-ε-Cl-Z-lysine resin (0.372 mole amino acid/g resin) was subjected to a deprotection-neutralization cycle using the following schedule:
(a) Three washes with methylene chloride
(b) Deprotection by treatment with 30% TFA (trifluoroacetic acid) in methylene chloride for 20 minutes.
(c) Three washes with methylene chloride
(d) Two washes with ethanol
(e) Three washes with methylene chloride
(f) Neutralization by 10% triethylamine in methylene chloride for 10 minutes
(g) Three washes with methylene chloride Threefold excess of the next amino acid in the sequence t-Boc-glycine and equivalent amount of dicyclohexyl carbodiimide in methylene chloride were used to acylate the amino group of lysine. After two hours coupling time a sample was removed to establish the completeness of the reaction by qualitative ninhydrin test. If incomplete, the coupling was repeated as described above. Upon completion of the coupling reaction, the peptide resin was washed three times with ethanol. The peptide resin was taken through deprotection-neutralization cycles and the t-BOC derivative of the next amino acid (in the appropriate side chain protected form) in sequence was coupled following the schedule described for the first amino acid.

Coupling of t-BOC-aspragine and t-BOC-glutamine was carried out in the presence of equivalent amount of 1-hydroxybenztriazole. The attachment of the last residue completed the synthesis. The peptide resin (7.3 g) was dried and treated with several drops of DMS (diamethylsulfide), 9 ml anisole and 70 ml liquid HF in an HF (hydrogen fluoride) apparatus. The cleavage reaction proceeded for 60 minutes at 0° C. after which the HF was removed under reduced pressure. The remaining material was washed with ether, and was extraced with 60 ml of 50% acetic acid and 240 ml of water. Lyophilization gave 2.2 g crude, deprotected undecapeptide.

The first step of purification was by CCD (counter current distribution) using the solvent system n:butanol:acetic acid:water:ethanol in 4:1:5:0.02 ratio. After 200 transfers tubes 39–59 were pooled to yield 1.2 g material. It showed some tailing by TLC (thin layer chromatography) in the solvent system acetic acid:ethyl acetate:water:n:butanol 1:1:1:1. This product was further purified on SG 50 column by partition chromatography and eluted with the upper phase of the solvent system n-butanol:acetic acid:water 4:1:5. One hundred fifty-six (156) mg pure peptide was secured which proved to be pure by HPLC, TLC, amino acid analysis and paper electrophoresis.

Each of the peptides of the present invention may be prepared by an analogous procedure by the stepwise addition of the desired amino acid to the growing peptide chain which is bound by a covalent bond to the solid resin.

EXAMPLE 2

Preparation of Pro-Asp-Ala-Arg-His-Ser 5 g of α-t-BOC-Ser (OBzl) resin (0.46 mmole amino acid/g resin) was subjected to deprotection, neutralization and coupling cycles following the schedule described for Example 1. Four molar excess of dicyclohexyl carbodiimide and the protected amino acids histidine, arginine, alanine, aspartic acid and proline were used in the subsequent coupling steps.

The completeness of the coupling reactions were established by the semi-quantitative ninhydrin test on a small sample. After completion of the last coupling reaction, the dry peptide resin (6.8 g) was placed into the reaction vessel of the HF cleavage apparatus and was treated with 60 ml of liquid HF and 6 ml of anisole at 0° C. for 60 minutes. After extraction and lyophilization 1.5 g crude peptide was isolated. The entire batch was applied to purification by CCD (counter current distribution) using the solvent system n-butanol:acetic acid:water in 4:1:5 ratio. After 200 transfers 1.35 g material was collected from tubes 6-24. This product was found to be pure by thin layer chromatography, high pressure liquid chromatography, paper electrophoresis and amino acid analysis.

EXAMPLE 3

Preparation of the tetradecapeptide Ser-Val-Met-His-Glu-Ala-Leu-His-Asn-His-Tyr-Thr-Gln-Lys 3.65 g α-t-BOC-ε-Cl-Z-lysine resin (0.414 mmole/g resin) was put through deprotection and neutralization cycles as described for EXAMPLE 1. Four equivalents of t-BOC-glutamine, DCC (dicyclohexylcarbodiimide) and 1-Hydroxybenztriazole were used in the next coupling cycle. The appropriately protected amino acid residues corresponding to the primary sequence were coupled in subsequent steps to give 7.4 g of the protected tetradecapeptide resin. HF cleavage was effected by addition of 5.0 ml anisole, a few drops of dimethylsulfide and 40 ml of liquid HF and stirring the mixture at 0° C. for 60 minutes. The HF was removed and the residual material was washed with diethyl ether and extracted with 60 ml of 50% aqueous acetic acid followed by 240 ml of water. The solution was lyophilized to give 1.8 g crude material, which was submitted to purification by counter current distribution using the solvent system n-butanol:acetic acid:water in ratio 4:1:5 in 270 transfers. The main fraction (tubes 26-37) were further purified by carboxymethyl cellulose ion exchange chromatography with a linear gradient (0.01–0.3M) of ammonium acetate buffer of pH 4.5. The material corresponding to the main peak was purified by partition chromatography on a Sephadex G25 gel column which provided the final produce. Purity of the tetradecapeptide was determined by HPLC, TLC, paper electrophoresis and amino acid analysis.

EXAMPLE 4

Purification of Ac-Gln-Pro-Glu-Asn

After HF cleavage, the crude material (400 mg) was applied to purification by CCD using the solvent system n-butanol:acetic acid:water in a 4:1:5 ratio. After 250 transfers, fractions 33-37 were pooled to give 53 mg of the pure product. This was found to be pure by thin layer chromatography, (solvent system nBuOH:Pyr:ACOH:H$_2$O, 1:1:1:1) high pressure liquid chromatography, paper electrophoresis and amino acid analysis.

EXAMPLE 5

Purification of Thr-Arg-Ala-Glu

The HF cleaved crude Thr-Arg-Ala-Glu (300 mg) was purified by a G-25 partition column using n-BuOH:HOAc:H$_2$O 4:1:5 upper layer as the eluent to afford partially purified Thr-Arg-Ala-Glu (163 mg). This peptide was further purified by reversed phase liquid chromatography (C-18, 40 micron) using 0.1% HOAc as the eluting solvent to afford pure Thr-Arg-Ala-Glu (54 mg).

EXAMPLE 6

Purification of Glu-Lys-Gln-Arg

Crude peptide was purified by counter-current distribution using n-BuOH:HOAc:H$_2$O (4:1:5) system to afford Glu-Lys-Gln-Arg. This peptide was purified by reversed phase liquid chromatography (C-18, 40 micron) using 0.1% HOAc to give the pure Gly-Lys-Gln-Arg.

EXAMPLE 7

Purification of Arg-Ser-Thr-Thr-Lys-Thr-Ser-Gly-Pro-Arg

The dry peptide resin (4.1 g) was placed into the reaction vessel of the HF cleavage apparatus and was treated with 40 ml of liquid HF and 5.0 ml of anisole at 0° C. for 60 minutes. After extraction and lyophilization 750 mg crude peptide was isolated.

The entire batch was purified by CCD (counter space current distribution) using the solvent system n-butanol::acetic acid:water in 4:1:5 ratio. After 220 transfers, fractions 81–85 were pooled to give 200 mg of the pure product. This product was purified by thin layer chromatography (solvent system n-butanol:Pyr:acetic acid:water, 15:10:13:12), and confirmed by high pressure liquid chromatography, paper electrophoresis, and amino acid analysis.

EXAMPLE 8

Purification of Asp-Lys-Ser-Arg

The dry peptide resin (7.3 g) was placed into the reaction vessel of the HF cleavage apparatus and was treated with 60 ml of liquid HF and 8 ml anisole at 0° C. for 60 minutes. After extraction and lyophilization approximately 1 g crude peptide was isolated.

The entire batch was purified by CCD (counter current distribution) using the solvent system n-butanol:acetic acid:water in 4:1:5 ratio. After 220 transfers, fractions 65 to 110 were pooled to give approximately 1 g of product. The product was purified by liquid chromatography using a cation exchange column and partition columns. The purified product was confirmed by amino acid analysis.

As used in the present specification and claims an active site peptide is a peptide with amino acid sequence derived from an immunoglobulin active site. An immunoglobulin active site is a portion of an immunoglobulin molecule which physically binds to an immunoglobulin Fc receptor, theeby triggering Fc receptor functions. An active site peptide, by virtue of its resemblance to a portion of an intact immunoglobulin molecule, is able to bind to an immunoglobulin Fc receptor and thereby mimic the intact immunoglobulin. Such binding may either stimulate or inhibit the specific immune function normally mediated by the receptor.

Lymphocytes

Lymphocytes are a class of leukocytes which constitute a portion of the "cellular arm" of the immune system. They are found circulating in peripheral blood, lymph fluid and in lymphoid tissues throughout the body including the spleen, thymus, lymph nodes, bone marrow and in other organs.

Lymphocytes have a central role in immune system development and defense. They function as regulators of the growth and development of leukocytes, as "killer" cells which directly attack infectious or foreign cells and as producers of immunoglobulins.

Lymphocytes may be divided into three broad classes; thymus-derived T lymphocytes (T cells), B lymphocytes (B cells) and lymphocytes lacking the characteristics of T and B cells, "null cells." B cells are the developmental precursors of immunoglobulin-producing plasma cells which synthesize all of the body's antibodies. T cells have two broadly defined functions which involve immume system regulation and direct killing of infectious or foreign cells. Regulatory T cells (T helper, T suppressor, T amplifier/inducer, etc.) regulate the growth and development of T and B lymphocytes and possibly other leukocytes. Such regulation is thought to be accomplished by T lymphocyte secretion of lymphokines, potent activating and growth regulatory molecules.

Certain classes of T cells also have direct cell killing abilities. Such killing may be aided by IgG bound antigens on the offending cell (antibody-dependent cell-mediated cytotoxicity (ADCC)) or may occur in an antibody-independent manner as in delayed-type hypersensitivity.

Null cells include those lymphocytes which can recognize and kill many cancerous cells without prior exposure to the cells. The null cells which mediate such spontaneous killing are termed natural killer cells (NK cells) and are thought to be important in protection against cancer.

Lymphocytes are also important activators and enhancers of the defensive function of leukocytes. Certain substances secreted by antigen-stimulated lymphocytes, for example, greatly enhance the bacteriocidal and tumoricidal activities of macrophages; other lymphoctye-derived substances attract various classes of leukocytes to the site of an immune response, thus enhancing the local defensive response.

Lymphocyte growth, development and activity is also regulated by regulatory molecules secreted by various lymphoid and non-lymphoid cells. These molecules include thymic hormones, interleukins, immunoglobulins and other molecules. Of central importance to the present invention is the ability of the various immunoglobulins to regulate the growth, development and activity of lymphocytes by interaction with lymphocyte FC receptors.

It is understood that various other modifications will be apparent to and can readily be made by those skilled in the art without departing from the scope and spirit of this invention. Accordingly, it is not intended that the scope of the claims appended thereto be limited to the description as set forth above, but rather that the claims be construed as encompassing all the features of patentable novelty which reside in the present invention, including all features which would be treated as equivalents thereof by those skilled in the art to which this invention pertains.

What is claimed is:

1. A peptide haveing an amino acid sequence

Arg-Ser-Thr-Thr-Lys-Thr-Ser-Gly-Pro-Arg composed of L-enantiomeric amino acid residues and pharmaceutically acceptable salts thereof.

* * * * *